(12) United States Patent
Mendelsohn et al.

(10) Patent No.: US 9,770,412 B2
(45) Date of Patent: Sep. 26, 2017

(54) IMPLANT DEVICE FOR DRUG DELIVERY

(71) Applicant: Nano Precision Medical, Inc., Emeryville, CA (US)

(72) Inventors: Adam D. Mendelsohn, Emeryville, CA (US); Kathleen Fischer, Emerville, CA (US); Tomoyuki Yoshie, Emeryville, CA (US)

(73) Assignee: NANO PRECISION MEDICAL, INC., Emeryville, CA (US)

( * ) Notice: Subject to any disclaimer, the term of this patent is extended or adjusted under 35 U.S.C. 154(b) by 0 days.

(21) Appl. No.: 15/113,165

(22) PCT Filed: Jan. 23, 2015

(86) PCT No.: PCT/US2015/012604
§ 371 (c)(1),
(2) Date: Jul. 21, 2016

(87) PCT Pub. No.: WO2015/112811
PCT Pub. Date: Jul. 30, 2015

(65) Prior Publication Data
US 2017/0000731 A1    Jan. 5, 2017

Related U.S. Application Data

(60) Provisional application No. 62/023,431, filed on Jul. 11, 2014, provisional application No. 61/930,534, filed on Jan. 23, 2014.

(51) Int. Cl.
*A61K 9/00* (2006.01)
*A61M 31/00* (2006.01)
*B82Y 30/00* (2011.01)

(52) U.S. Cl.
CPC .......... *A61K 9/0092* (2013.01); *A61K 9/0024* (2013.01); *A61M 31/002* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 4,341,834 A * | 7/1982 | Kikuchi | B23B 27/148 427/249.17 |
| 5,972,369 A | 10/1999 | Roorda et al. | |
| 8,158,034 B2 | 4/2012 | Kang et al. | |
| 2005/0214533 A1* | 9/2005 | Shimosaki | B01D 53/86 428/375 |
| 2008/0188836 A1* | 8/2008 | Weber | A61L 29/085 604/890.1 |
| 2009/0232870 A1 | 9/2009 | Srivastava et al. | |
| 2010/0187172 A1* | 7/2010 | Paulose | B82Y 30/00 210/506 |
| 2010/0213046 A1 | 8/2010 | Grimes et al. | |
| 2010/0269894 A1 | 10/2010 | Misra et al. | |
| 2013/0056702 A1* | 3/2013 | Wang | C23C 16/40 257/4 |
| 2014/0371687 A1 | 12/2014 | Mendelsohn et al. | |

FOREIGN PATENT DOCUMENTS

CN     101191248     6/2008
CN     101550581     10/2009

* cited by examiner

*Primary Examiner* — Robert A Wax
*Assistant Examiner* — Quanglong N Truong
(74) *Attorney, Agent, or Firm* — Kilpatrick Townsend and Stockton LLP (57) ABSTRACT

The present invention provides a method for controlling the internal diameter of nanopores to afford nanopore membranes with a zero-order rate of release of a therapeutic agent.

22 Claims, 11 Drawing Sheets

Membranes in prototype devices
18 months
Histology in situ

IMPLANT DEVICE FOR DRUG DELIVERY

CROSS-REFERENCES TO RELATED APPLICATIONS

This application is a U.S. national phase of PCT Application No. PCT/US2015/012604, filed on Jan. 23, 2015, which claims priority to U.S. Provisional Application Nos. 62/023,431, filed Jul. 11, 2014, and 61/930,534, filed Jan. 23, 2014, each of which is hereby incorporated by reference in its entirety for all purposes.

BACKGROUND OF THE INVENTION

Many treatments would benefit from a zero-order release rate, potentially improving efficacy and reducing side effects. Furthermore, a long-term, implantable device may reduce the number of unpleasant injections and improve compliance.

Because their pores are so similar in size to the molecules they deliver, nanoporous membranes have shown the ability to confine molecular diffusion, leading to a constant rate, non-Fickian drug release. However, most nanoporous membranes are made of silicon or alumina and attached to a reservoir using an adhesive; none of these materials are commonly used as a tissue-contacting surface in FDA-approved implantable devices.

In contrast, titanium and titanium oxide (titania) have been used for decades with an excellent record of biocompatibility. The manufacture of an all-titanium/titania membrane has been previously reported, including demonstration of zero-order diffusion in vitro, an expected in vivo pharmacokinetic profile, and data showing biocompatibility for over a year. What is needed, however, is a method for preparing nanopores where the internal diameter can be precisely controlled such that zero-order release can be achieved for any therapeutic agent. Surprisingly, the present invention meets this and other needs.

BRIEF SUMMARY OF THE INVENTION

In one embodiment, the present invention provides a method of preparing a coated nanoporous membrane having a plurality of nanopores, wherein each nanopore has a first open end and an interior, the method including forming a reaction mixture under vapor deposition conditions in a reaction chamber wherein the reaction mixture includes a coating agent and the nanoporous membrane, such that a portion of the interior of each nanopore is coated with the coating agent to form a coating layer.

In another embodiment, the present invention provides a nanopore comprising a coated interior portion prepared by the method of the present invention.

In another embodiment, the present invention provides a nanopore membrane including a plurality of nanopores, each nanopore having a first open end and an interior, wherein at least one nanopore comprises a coating layer on a portion of the interior portion.

In another embodiment, the present invention provides a capsule suitable for implantation, a reservoir encapsulated by the capsule, wherein the reservoir is suitable for containing a therapeutic agent, and a nanopore membrane attached to the capsule such that the nanopore membrane is in contact with the reservoir, wherein the nanopore membrane includes a plurality of nanopores in fluid contact with the reservoir, wherein the nanopores have an interior with a coating layer on at least a portion of the interior, such that the plurality of nanopores is a diffusion pathway out of the reservoir for the therapeutic agent.

In some embodiments, the present invention provides a titania composition having a titanium substrate, an amorphous titania layer on the titanium substrate, wherein the titania layer includes $TiO_xC_y$, wherein subscript x is from about 1.5 to about 4.0, and subscript y is from 0 to about 1.0, and at least one layer of $TiO_x$ chemically bound to the amorphous titania layer, wherein subscript x is from about 1.5 to about 4.0.

BRIEF DESCRIPTION OF THE DRAWINGS

FIGS. 14A, B & C show a schematic of nanotube membrane delivery device. FIG. 14A) Vertically aligned nanotube membrane controls flow of molecules. FIG. 14B) Membranes are combined with a reservoir device and loaded. FIG. 14C) Overview of full device.

FIGS. 16A and B show filling capacity for different devices. FIG. 16A) Thin, 2 mm device, with length varying from 0.2 cm to 4 cm. FIG. 16B) Long, 4 cm device, with diameter varying from 0.7 to 4 mm. On both, concentrations from 50 mg/ml to 800 mg/ml are plotted as different lines (♦—50 mg/ml, ■—200 mg/ml, ▲—500 mg/ml, ✖—800 mg/ml).

DETAILED DESCRIPTION OF THE INVENTION

I. General

The present invention provides a method of coating a portion of the interior of nanopores and nanotubes with an atomic layer of a material. Using vapor deposition conditions, such as Atomic Layer Deposition (ALD) conditions, the coating of a portion of the interior of the nanopores and nanotubes can be controlled. The interior of the nanopores and nanotubes can be coated uniformly, or form a gradient from one end to the other of the nanopore or nanotube. The coating of the nanopores allows the internal diameter of the nanopores to be more precisely controlled so that a zero-order release rate can be achieved for any given therapeutic agent.

II. Definitions

"Nanopore membrane" or "nanoporous membrane" refers to an array of nanopores where at least a portion of the nanopores are open at both ends and capable of allowing diffusion of liquids or solids from one side of the membrane to the other through the nanopores. The nanopore membrane can be a nanotube membrane when the nanopores are nanotubes. The nanopores can include a variety of shapes such as nanotubes, such that the nanopore membrane can be a nanotube membrane. When the nanopores or nanotubes are prepared from titanium, a titanium nanopore membrane or a titanium nanotube membrane can be formed.

"Forming a reaction mixture" refers to the process of bringing into contact at least two distinct species such that they mix together and can react. It should be appreciated the resulting reaction product can be produced directly from a reaction between the added reagents or from an intermediate from one or more of the added reagents which can be produced in the reaction mixture.

"Vapor deposition conditions" refers to the combination of temperature, pressure, gas flow, and reagent that enable the vapor phase deposition of a metal or other coating agent. These conditions include conditions for deposition of the metal or coating agent one atomic layer at a time, i.e, Atomic Layer Deposition.

"Reaction chamber" refers to any chamber suitable for vapor deposition, such as a metal vacuum chamber including a heating element and multiple gas inlet and outlet lines.

"Coating agent" refers to an agent capable of depositing a single atom of a metal or other element. Examples of coating agents include, but are not limited to, metal complexes, metal salts, and other forms of metal or substances to be deposited. The coating agent can also include tetrakis (dimethylamido)titanium (TDMAT). The coating agent can include the same metal as the nanopore membrane being coated, or a different metal.

"Coating layer" refers to the layer resulting from vapor deposition of the coating agent onto the nanopore membrane. The coating layer can be bound to the underlying nanopore membrane by any suitable means such as by forming a covalent bond directly or via intervening atoms, ionic bonding, by Van der Waal's forces, or a combination thereof. The coating layer can have a uniform coating thickness in the pores of the nanopore membrane, or form a gradient with an increasing or decreasing thickness progressing from one end of the nanopore to the other. When the coating agent includes titanium, the coating layer can be titania, thus forming a titania layer that can be chemically bound to the nanopore membrane.

"Titania" and "titanium oxide" refers to the oxide of titanium, $TiO_x$, where subscript x can be about 2, such as 1.8 to 2.2, and all fractions in between, or $TiO_2$. Titania also includes compositions having other ratios of titanium and oxygen, such as where subscript x is from about 1.5 to about 4.0, such as about 3.0. The titania can also include other elements, such as carbon, forming $TiO_xC_y$, wherein x is from about 1.5 to about 4.0, and y is from 0 to about 1.0.

"Amorphous" refers to a non-crystalline solid.

"Substrate" refers any material which can be support a nanopore membrane. Examples of suitable substrates include, but are not limited to, glass (including controlled-pore glass), polymers (e.g., polystyrene, polyurethane, polystyrene-divinylbenzene copolymer), silicone rubber, quartz, latex, metals including transition metals such as titanium, magnetic materials, silicon dioxide, silicon nitride, gallium arsenide, and derivatives thereof.

"Purging" refers to removing the gaseous contents of the reaction chamber.

"Therapeutic agent" refers to any agent capable of providing a therapeutic response, such as a drug or biologic.

"Fluid contact" refers to the contents of the reservoir being able to diffuse from the reservoir to the titania nanotubes. The contents of the reservoir can be in liquid form, but can also be in powder or solid form.

III. Method of Making a Coated Nanoporous Membrane

The present invention describes a method of preparing a coated nanoporous membrane by coating the interior portion of the nanopores with a coating agent under vapor deposition conditions. In some embodiments, the present invention provides a method of preparing a coated nanoporous membrane having a plurality of nanopores, wherein each nanopore has a first open end and an interior, the method including forming a reaction mixture under vapor deposition conditions in a reaction chamber wherein the reaction mixture includes a coating agent and the nanoporous membrane, such that a portion of the interior of each nanopore is coated with the coating agent to form a coating layer.

Some nanopores of the nanoporous membrane have a first end and a second end, both of which are open. The nanopores have an interior portion that can be coated during the method of the present invention. The internal diameter of the nanopores, the diameter at the first or second end of the nanopores, decreases at least one of the first and second ends after deposition of the coating layer. The internal diameter is the diameter of the portion of the nanopore through which the therapeutic agent can diffuse or exit. The external diameter of the nanopore is the distance across the nanopore from the point of contact with an adjacent nanopore to the point of contact with another adjacent nanopore. The external diameter includes the internal diameter plus the thickness of any coating layer plus the thickness of the nanopore wall itself.

The vapor deposition conditions of the present invention are those conditions that enable the deposition of the coating agent in a gaseous form. This combination of conditions can include pressure, temperature, gas composition, gas flow, time of deposition, and other factors. Any suitable pressure can be used in the method of the present invention. For example, the pressure can be greater than atmospheric pressure, about atmospheric pressure, or less than atmospheric pressure. In some embodiments, the pressure can be less than atmospheric pressure. When the pressure is less than atmospheric pressure, the pressure can be less than about 1.0 bar, $1.0 \times 10^{-1}$, $1.0 \times 10^{-2}$, $1.0 \times 10^{-3}$, $1.0 \times 10^{-4}$, or $1.0 \times 10^{-5}$ bar, or less.

Any suitable temperature can be used in the method of the present invention. For example, the temperature can be less than about 500° C., or 400, 300, 200, or less than about 100° C. In some embodiments, the temperature is sufficient to maintain the nanopore membrane in a crystalline state. In some embodiments, the temperature can be less than about 120° C. In some embodiments, the temperature can be less than about 100° C. In some embodiments, the temperature is sufficient to maintain the nanopore membrane in an amorphous state.

Any suitable carrier gas can be used to assist the preparation of the coated nanoporous membranes. The carrier gas helps introduce the coating agent to the reaction chamber and to remove products of the reaction from the reaction chamber. The carrier gas can be any suitable gas, such as argon or nitrogen, or other inert gas. The carrier gas can be used at any suitable flow rate from about 0.01 sccms to about 1000 sccms. In some embodiments, the carrier gas can be argon.

Any suitable time can be used in the method for coating the nanoporous membrane. For example, the coating time can be less than about 1 minute to more than 1 hour. In some embodiments, the coating time can be about 1 second, or about 5, 10, 15, 20, 25, 30, 35, 40, 45, 50, 55, 60, 70, 80, 90, or about 100 seconds. In some embodiments the coating time can be about 1 minute, or 2, 3, 4, 5, 10, 15, 20, 30, 45 or about 60 minutes or more.

The vapor deposition conditions of the present invention also include conditions for atomic layer deposition of the coating agent. In some embodiments, the vapor deposition conditions can be Atomic Layer Deposition conditions. Atomic Layer Deposition conditions can include any suitable temperature, such as from about room temperature to about 100° C. For example, the temperature can be room temperature, or from about 30° C., 40, 50, 60, 70, 80, 90° C. to about 100° C. In some embodiments, the Atomic Layer Deposition conditions comprise a temperature of from about room temperature to about 100° C. In some embodiments, the Atomic Layer Deposition conditions comprise a temperature of from about 50° C. to about 100° C. Atomic Layer Deposition conditions can include any suitable pressure.

The reaction mixture can include any suitable components, including the nanoporous membrane and the coating agent. Any suitable nanoporous membrane can be used in the method of the present invention. See, for example, U.S. Publication No. 2014/0371687, describing the preparation of nanoporous membranes useful in the present invention. The nanoporous membranes can be any suitable material. For example, the nanoporous membrane can be titania. The nanoporous membrane can also include any suitable number of nanopores, including at least $10^0$, $10^1$, $10^2$, $10^3$, $10^4$, $10^5$, $10^6$, or at least about $10^7$ nanopores.

Any suitable coating agent can be used in the method of the present invention. The coating agent can be chosen to prepare a coating layer of the same or similar composition of the nanoporous membrane. Alternatively, the coating agent can be chosen to prepare a coating layer of a different composition than the nanoporous membrane. Coating agents useful in the method of the present invention are reactive with the nanoporous membrane but not with itself, and are in the gaseous phase under the vapor deposition conditions of the present invention. The coating agent can be any suitable precursor for the metal or other material to be deposited. For example, the coating agent can include titanium when the coating layer includes titania. In some embodiments the coating agent includes titanium. For example, the coating agent can be tetrakis(dimethylamido) titanium (TDMAT), titanium isopropoxide (TTIP), or titanium tetrachloride ($TiCl_4$), to prepare a titania coating layer. In some embodiments, the coating agent can be tetrakis (dimethylamido)titanium (TDMAT). In some embodiments, the coating layer includes titania. When the coating layer is titania, the titania can be any suitable composition generally represented by $TiO_x$, where subscript x can be from about 1.5 to about 4.0, or from about 2.5 to about 3.5, or from about 1.8 to about 2.2.

The coating layer can be any suitable thickness. For example, the coating layer can have a thickness of from about 1 nm to about 100 nm, or about 5, 10, 15, 20, 25, 30, 40, 50, 60, 70, 80, 90 or about 100 nm. The coating layer can have a uniform thickness from one end of the nanopore to the other, or the thickness can vary. In some embodiments, the coating layer may coat only a portion of the interior of the nanopores and not extend to the other end of the nanopores. In some embodiments, the coating layer can extend from one end of the nanopore interior to the other end, completely coating the nanopore interior.

Any suitable reaction chamber can be used in the method of the present invention. The reaction chambers useful in the method of the present invention can tolerate the vapor deposition conditions used to prepare the coated nanoporous membranes, including the temperatures and pressures. Moreover, the reaction chambers are configured to allow gas to enter and exit the chamber while maintaining a constant pressure. Suitable materials for the reaction chamber include metals.

The nanopores of the membranes of the present invention can have any suitable dimensions, including the internal diameter, the length and the aspect ratio. The internal diameter can be from about 1 nm to about 1000 nm, and can be the same or variable along the length of the nanopore. When the internal diameter is variable, the internal diameter can increase from one end of the nanopore to the other. For example, the internal diameter of the nanopore at the end in contact with the reservoir can be smaller than at the end opposite the reservoir, where the internal diameter increases gradually along the length of the nanopore. The internal diameter can be about 1, 2, 3, 4, 5, 6, 7, 8, 9, 10, 15, 20, 25, 30, 35, 40, 45, 50, 75, 100, 200, 300, 400, 500 or 1000 nm. The internal diameter can be of from about 1 to 1000 nm, or from about 1 to about 100 nm, or from about 1 to about 50 nm, or from about 1 to about 20 nm. In some embodiments, the internal diameter can be of from about 10 nm to about 1000 nm.

The nanopores can have any suitable length. For example, the nanopores can be from about 100 nm to about 100 μm, or about 500 nm, 1 µm, 5, 10, 20, 30, 40, 50, 60, 70, 80, 90 or 100 µm. In some embodiments, the nanopores have a length of about 1 µm to about 100 µm.

The nanopores can also have any suitable aspect ratio, defined by the length of the nanopore divided by the internal or external diameter. The aspect ratio can be from about 10 to about 10,000, or from about 10 to about 1,000. Other aspect ratios include, but are not limited to, about 50, 100, 200, 300, 400, 500, 600, 700, 800, 900, 1000, 2000, 3000, 4000, 5000, 6000, 7000, 8000, 9000, or 10,000.

The interior portion of the nanopores can be coated to any suitable degree. For example, at least 10% of the interior portion of the nanopores can be coated, or 20, 25, 30, 35, 40, 45, 50, 55, 60, 65, 70, 75, 80, 85, 90 or at least 95% of the interior portion of the nanopores can be coated. The interior portion of the nanopores can also be coated with a uniform thickness of the coating layer, or asymmetrically so that one end of the nanopore interior has a different thickness of the coating layer than the other end of the nanopore interior. The degree of coating, as well as the nature of the coating, uniform or asymmetric coating, can be controlled by the vapor deposition conditions.

The nanopores can be any suitable material, as described for the nanoporous membrane. In some embodiments, the plurality of nanopores include titania. The nanopores can also adopt any suitable physical form, such as crystalline, amorphous, or a combination thereof. In some embodiments, the plurality of nanopores are substantially amorphous. In some embodiments, the nanopores can be amorphous titania. The titania nanopores can have any suitable composition generally represented by $TiO_x$, where subscript x can be from about 1.5 to about 4.0, or from about 2.5 to about 3.5, or from about 1.8 to about 2.2. The titania nanopores can include other components as well, depending on how the nanopores are prepared. In some embodiments, the titania nanopores can include $TiO_xC_y$, wherein subscript x can be from about 1.5 to about 4.0, or from about 2.5 to about 3.5, or from about 1.8 to about 2.2, and subscript y can be from 0 to about 1.0, or from about 0.1 to about 1.0, or from about 0.5 to about 1.0, or about 0.75. In some embodiments, the titania nanopores can include $TiO_xC_y$, wherein subscript x can be from about 1.5 to about 4.0, and subscript y can be from 0 to about 1.0. In some embodiments, the titania nanopores can include $TiO_xC_y$, wherein subscript x can be from about 2.5 to about 3.5, and subscript y can be from about 0.5 to about 1.0.

In some embodiments, the plurality of nanopores can be nanotubes such that the nanoporous membrane can be a nanotube membrane. When the nanopores are nanotubes, the nanotubes can be coated to any suitable degree, as described above for the nanopores. In some embodiments, at least 10% of each nanotube interior is coated. In some embodiments, at least 50% of each nanotube interior is coated. In some embodiments, at least 75% of each nanotube interior is coated.

The nanotubes of the present invention can also have any suitable dimensions, as described above for the nanopores. In some embodiments, the plurality of nanotubes before the forming step have an internal diameter of between 10 nm to 200 nm. In some embodiments, the plurality of nanotubes after the forming step have an internal diameter of between 1 nm to 100 nm.

Any suitable substrate can be used to support the nanotube membrane of the present invention. The substrate can be a metal, ceramic, polymer, glass, semiconductor, or mixture thereof. In some embodiments, the nanotube membrane is in contact with a substrate. In some embodiments, the substrate can include titanium.

The method of the present invention can include any other suitable material or component in the process of coating the nanoporous membrane. For example, the reaction mixture can also include water vapor.

The steps of the present invention can be practiced in any particular order, and be repeated any number of times to prepare the coated nanotube membrane of the present invention. When the forming step is repeated, it can be useful to first purge the reaction chamber of any carrier gases, coating agents, or any other material, before repeating the forming step. In some embodiments, the method can include purging the reaction chamber of the coating agent, and repeating the forming step. When the forming step is repeated, the coating agent can be the same coating agent used in the previous forming step, or can be different.

Any suitable number of cycles can be used to form the coating layer of the present invention. For example, a single cycle of coating the nanoporous membrane can be used. Alternatively, more than one cycle of coating can be used, such as 2, 3, 4, 5, 10, 15, 20, 25, 30, 40, 50, 100, 200, 300, 400, 500, 600, 700, 800, 900, 1000 or more cycles can be used to prepare the coated nanoporous membrane of the present invention. In addition to the coating step described above, each cycle can also include the step of purging the reaction chamber so that a new coating agent can be introduced to the reaction chamber. The purging step can be performed for about 1 second, or about 5, 10, 15, 20, 25, 30, 35, 40, 45, 50, 55, 60, 70, 80, 90, or about 100 seconds. In some embodiments the purging step can be performed for about 1 minute, or 2, 3, 4, 5, 10, 15, 20, 30, 45 or about 60 minutes or more. The total time for depositing the coating layer, including one or more coating steps and one or more purging steps, can be from about 1 minute, or 5, 10, 15, 30, 45, or 60 minutes, or about 1 hour, or 2, 3, 4, 5, 6, 7, 8, 9, 10, 12, 16, or 24 hours, or longer.

Each cycle of coating the nanoporous membrane can deposit any suitable amount of the coating layer. For example, each coating step can deposit at least about 0.1 Å, or at least about 0.2, 0.3, 0.4, 0.5, 0.6, 0.7, 0.8, 0.9 or at least about 1.0 Å of the coating layer. The amount of the coating layer deposited in each coating step can different from other coating steps in the same sequence, such that later depositions of coating layers are thicker, or thinner, than earlier depositions of coating layers.

Without being bound by any theory, the nanopore membrane prior to being coated can include a matrix of amorphous titania, $TiO_xC_y$. The amorphous titania has many benefits, including improved adhesion to the titanium substrate. The coating process of the present invention can deposit a layer of titanium atoms on top of the titania matrix forming the nanopore membrane, such that the titanium is chemically bonded to the titania matrix of the nanopore membrane via oxygen atoms, such that the resulting coating layer can be titania. The coating process can be repeated to deposit additional layers of titania bound to the previous layer of titania.

In some embodiments, the coated nanotube membrane can be a titania nanotube membrane having a plurality of titania nanotubes, the method including forming the reaction mixture under Atomic Layer Deposition conditions in the reaction chamber wherein the reaction mixture includes the coating agent tetrakis(dimethylamido)titanium (TDMAT), and a titania nanotube membrane on a titanium substrate, such that at least a portion of the interior of the titania nanotube is coated with the titania coating agent to form the titania coating layer. In some embodiments, the method also includes forming a second reaction mixture under Atomic Layer Deposition conditions including a second coating agent and the nanoporous membrane, such that a portion of the interior of a second nanopore is coated with the second coating agent. The second coating agent can be any suitable coating agent, as described above. For example, the second coating agent can be the same or different than the first coating agent. In some embodiments, the second coating agent is the same as the first coating agent. In some embodiments, the second coating agent can be tetrakis (dimethylamido)titanium (TDMAT). In some embodiments, the second coating agent can be different than the first coating agent.

In some embodiments, the present invention provides a nanopore comprising a coated interior portion prepared by the method of the present invention.

In some embodiments, the present invention provides a nanopore membrane including a plurality of nanopores, each nanopore having a first open end and an interior, wherein at least one nanopore comprises a coating layer on a portion of the interior. The nanopores are described in more detail above.

In some embodiments, the present invention provides a titania composition having a titanium substrate, an amorphous titania layer on the titanium substrate, wherein the titania layer includes $TiO_xC_y$, wherein subscript x is from about 1.5 to about 4.0, and subscript y is from 0 to about 1.0, and at least one layer of $TiO_x$ chemically bound to the amorphous titania layer, wherein subscript x is from about 1.5 to about 4.0. The chemical bonding of the at least one layer of TiOx to the amorphous titania layer can be through any suitable chemical bond. In some embodiments, the at least one layer of TiOx is chemically bound to the amorphous titania layer through oxygen bridges between the titanium atoms in the at least one layer of TiOx and the amorphous titania layer.

IV. Devices

The present invention also includes a device having a nanoporous membrane prepared by the methods of the present invention, where the nanoporous membrane includes nanopores having a coating layer on the interior portion of the nanopores. In some embodiments, the present invention provides a capsule suitable for implantation, a reservoir encapsulated by the capsule, wherein the reservoir is suitable for containing a therapeutic agent, and a nanopore membrane attached to the capsule such that the nanopore membrane is in contact with the reservoir, wherein the nanopore membrane includes a plurality of nanopores in fluid contact with the reservoir, wherein the nanopores have an interior with a coating layer on at least a portion of the interior, such that the plurality of nanopores is a diffusion pathway out of the reservoir for the therapeutic agent.

Figure 13:
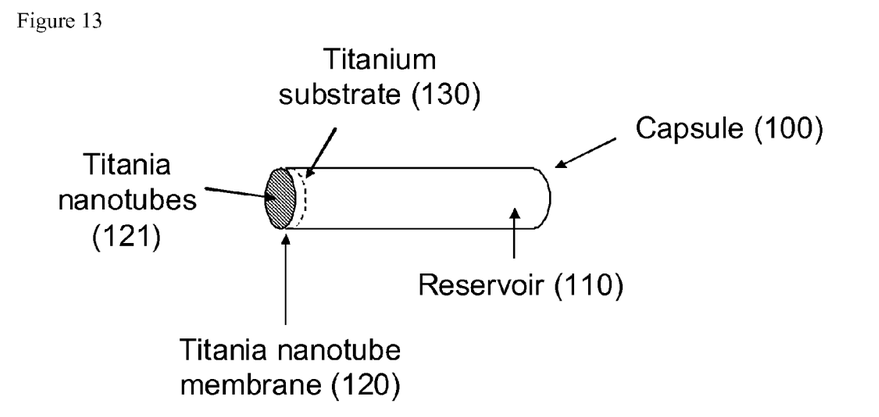
FIG. 13 shows one embodiments of the device of the present invention, with a capsule (100), a reservoir (110) encapsulated by the capsule, a titania nanotube membrane (120) in contact with the reservoir, where the titania nanotube membrane is on a titanium substrate (130), and where the titania nanotube membrane includes a plurality of titania nanotubes (121).
Figure 14A:
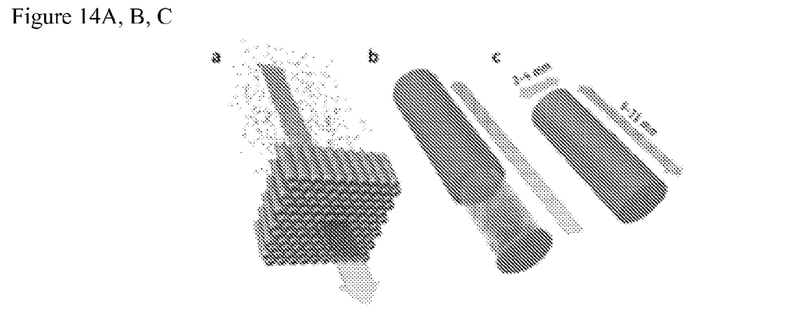

The capsule (100) of FIG. 13 can be any capsule that is biocompatible with the body. The capsule can be prepared from any suitable material such as metals, polymers and combinations thereof. Useful metals can be pure metals or alloys, and include, but are not limited to, titanium and steel. Polymers useful in the present invention include any natural or synthetic polymer that is biocompatible with the body. In some embodiments, the capsule includes titanium.

The reservoir can be any suitable volume and dimensions sufficient to release the therapeutic agent at a constant rate for the given interval.

The capsule can have any suitable shape or size. The capsule can be spherical, elliptical, oblong, circular, or cylindrical, among others, or a combination thereof.

The device also includes the reservoir (110) of FIG. 13 which contains the therapeutic agent. Any therapeutic agent is useful in the device of the present invention. The therapeutic agent can be in any suitable form in the reservoir, such as a liquid, a solid or a suspension. Solid forms include, but are not limited to, powders and micronized particles. For example, the powder can be lyophilized.

The titanium substrate (130) of FIG. 13 can be attached to the capsule by any suitable methods in the art. For example, the titanium substrate can be laser welded to the capsule.

The titania nanotubes (121) of FIG. 13 can have any suitable dimensions, including the internal diameter, the length and the aspect ratio. The internal diameter can be from about 1 nm to about 1000 nm, and can be the same or variable along the length of the titania nanotube. When the internal diameter is variable, the internal diameter can increase from one end of the titania nanotube to the other. For example, the internal diameter of the titania nanotube at the end in contact with the reservoir can be smaller than at the end opposite the reservoir, where the internal diameter increases gradually along the length of the titania nanotube. The internal diameter can be about 1, 2, 3, 4, 5, 6, 7, 8, 9, 10, 15, 20, 25, 50, 75, 100, 200, 300, 400, 500 or 1000 nm. The internal diameter can be of from about 1 to 1000 nm, or from about 1 to about 100 nm, or from about 1 to about 50 nm, or from about 1 to about 20 nm. In some embodiments, the internal diameter can be of from about 10 nm to about 1000 nm.

The titania nanotubes can have any suitable length. For example, the titania nanotubes can be from about 100 nm to about 100 µm, or about 500 nm, 1 µm, 5, 10, 20, 30, 40, 50, 60, 70, 80, 90 or 100 µm. In some embodiments, the titania nanotubes have a length of about 1 µm to about 100 µm.

The titania nanotubes can also have any suitable aspect ratio, defined by the length of the titania nanotube divided by the internal or external diameter. The aspect ratio can be from about 10 to about 10,000, or from about 10 to about 1,000. Other aspect ratios include, but are not limited to, about 50, 100, 200, 300, 400, 500, 600, 700, 800, 900, 1000, 2000, 3000, 4000, 5000, 6000, 7000, 8000, 9000, or 10,000.

The titania nanotubes are in fluid contact with the reservoir such that the therapeutic agent, whether in liquid, solid or suspension form, can diffuse from the reservoir and into the titania nanotubes at the titanium substrate, followed by exiting the titania nanotubes at the opposite end and entering the body. The rate of release of the therapeutic agent can be any suitable rate of release, such as zero-order rate of release. In some embodiments, the release of the therapeutic agent from the reservoir and through the titania nanotube membrane is a zero-order rate of release.

The titania nanotube membrane can be prepared by any suitable method. In some embodiments, the titania nanotube membrane is prepared by the method of the present invention.

The nanopore membrane is described in more detail above. Prior to coating the interior portions of the nanopore membrane as described above, the nanopore membrane can be prepared by methods known to one of skill, such as those described in U.S. Publication No. 2014/0371687. The nanopores of the present invention can be in fluid contact with the reservoir. In some embodiments, the plurality of nanopores is the only diffusion pathway out of the reservoir for the therapeutic agent.

V. Examples

Example 1. Preparation of a Coated Nanoporous Membrane

In this example, the implantable device is composed of a drug reservoir with a nanoporous membrane attached at one or both ends. The membrane and device are produced from titanium; once fully assembled, the only material in contact with the body is titanium oxide. Because of the uniform material characteristics, and the inherent biocompatibility of titanium oxide, there is a negligible immune response to the implant (see Biocompatibility section). Furthermore, since there are no moving parts or additional materials, the failure modes of this system are fewer than many other comparable implantable devices.

Constant-rate delivery is produced by having a pore that is appropriately matched in size to the drug molecule. The nanoporous membranes of the present invention can be produced with pore sizes from ones of nanometers to tens of nanometers with angstrom-scale precision, allowing constant-rate delivery of a range of molecules, from small molecules and peptides to antibodies and blood-clotting factors.

Preparation of Nanoporous Membranes

Nanoporous membranes are produced in three steps. Solid titanium disks are machined with blind holes, referred to as windows, on one side and a flat surface on the other. These membranes then undergo electrochemical anodization, producing a layer of titania nanotubes on the flat side of the disk. As grown, the titania nanotubes are closed at the interface with the titanium. An inductively-coupled plasma (ICP) deep etch is used to remove any remaining material, thus opening the bottoms of the nanotubes and producing a membrane structure with a nanotube layer on one side and a titanium support structure on the other side. Nanotubes on the nanopore membranes are 50 μm long and can be produced with pore diameters ranging from 1 nm to 50 nm at the narrow end, where the bottom of the nanotubes was in contact with titanium.

The membranes are welded to the reservoirs, producing the full device. Helium leak tests have shown a hermitic seal, with a leak rate of less than $10^{-10}$ torr. Since the nanotubes are grown from the surface of the titanium disk, there is no space between nanotubes and titanium at the interface. As a result, after device assembly, the only exit for molecules is through the nanotubes; furthermore, assembly is achieved without adhesives or additional materials (aside from titanium and titanium dioxide).

Coating of Nanoporous Membrane

To produce different pore sizes, layers of titanium oxide are deposited onto the surface of the nanotubes using atomic layer deposition (ALD). The deposition rate of titania remained constant at 0.69 Å/cycle across the number of cycles, giving very fine-tuned resolution for pore diameter. For example, after placing the substrate in the vacuum chamber, the substrate is heated to 80° C. Water vapor is added to the vacuum chamber at a temperature of 20° C., and TMDAT at a temperature of 70° C. The soaking time is 90 seconds, after which the vacuum chamber is pumped free of all gas for about 2 minutes.

Figure 1:
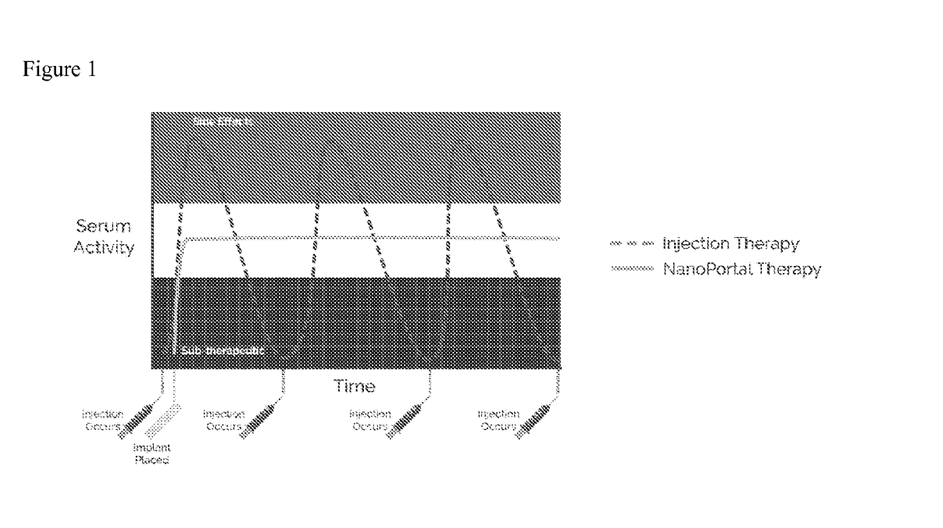
FIG. 1 shows one embodiment of a comparison between the present invention and injection therapy.
Figure 2:
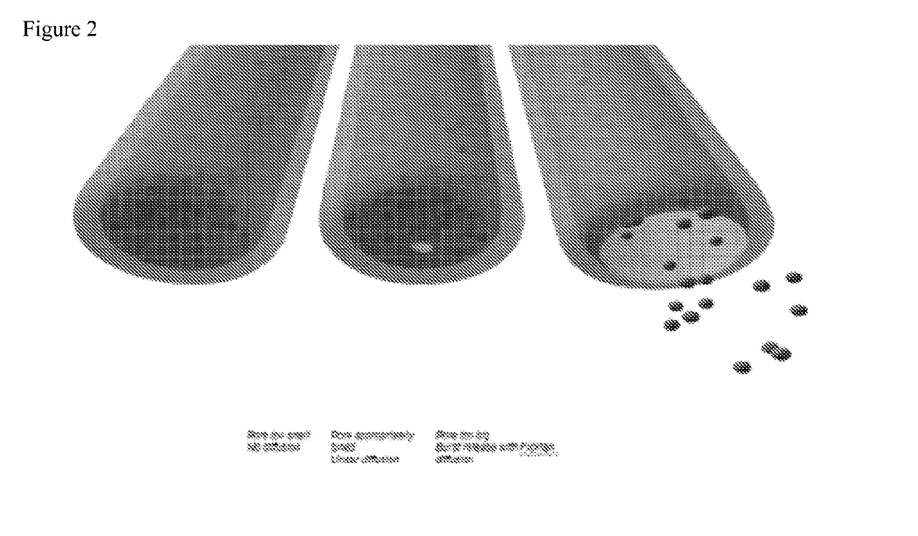
FIG. 2 shows one embodiment of a comparison of pore sizes.
Figure 3:
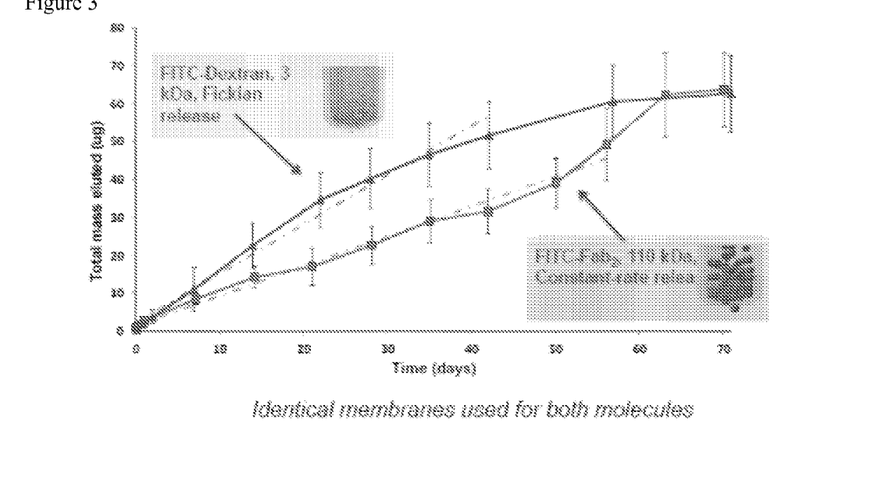
FIG. 3 shows one embodiment of the results from fluorescein isothiocyanate-Dextran 3 kDa (FITC-Dextran 3 kDa) and isothiocyanate conjugated antibody fragment ($Fab_2$) of 110 kDa.
Figure 4:
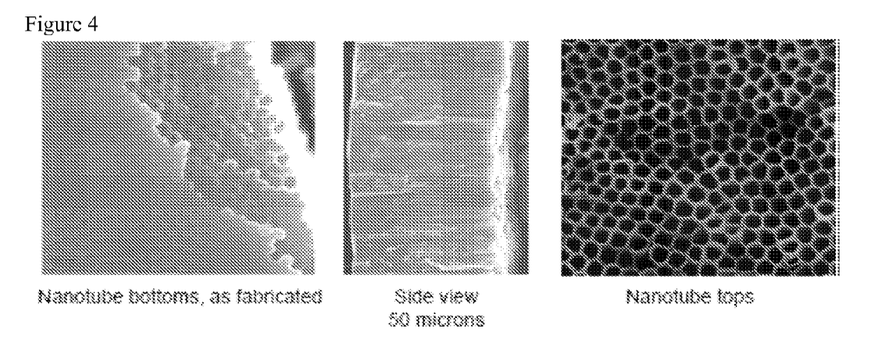
FIG. 4 shows one embodiment of nanotubes of the present invention.
Figure 5:
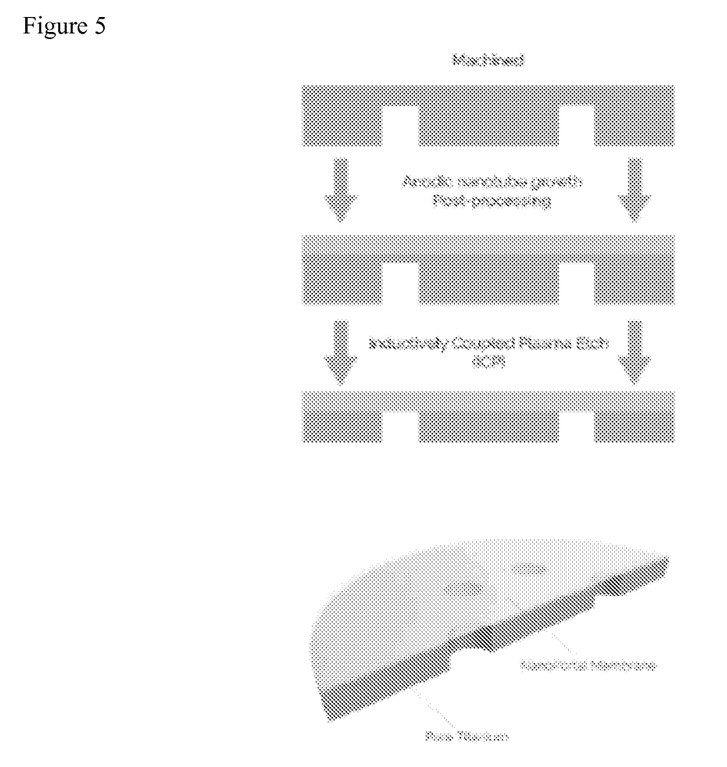
FIG. 5 shows one embodiment of a fabrication process of the present invention.
Figure 6:
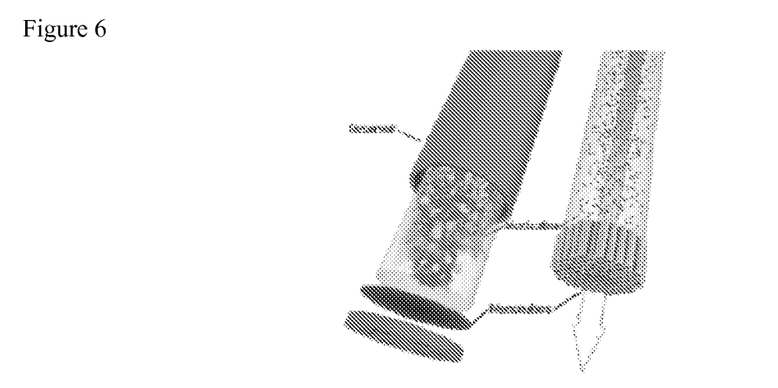
FIG. 6 shows one embodiment of a device of the present invention.
Figure 7:
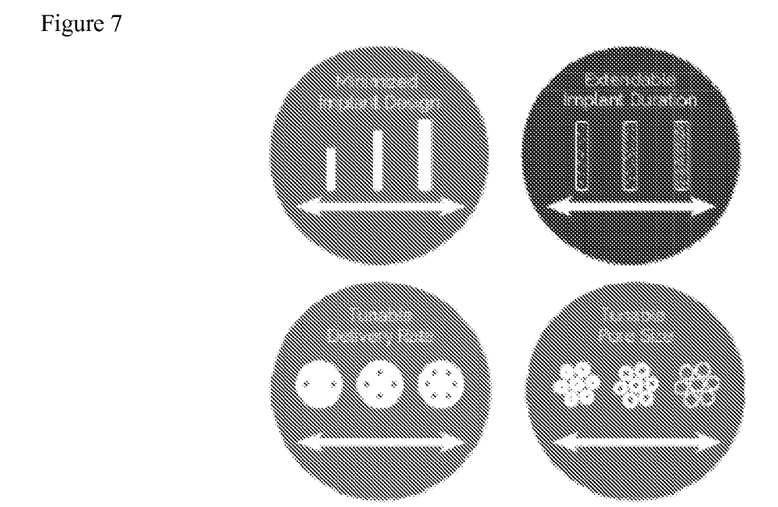
FIG. 7 shows one embodiment of features of a device of the present invention.
Figure 8:
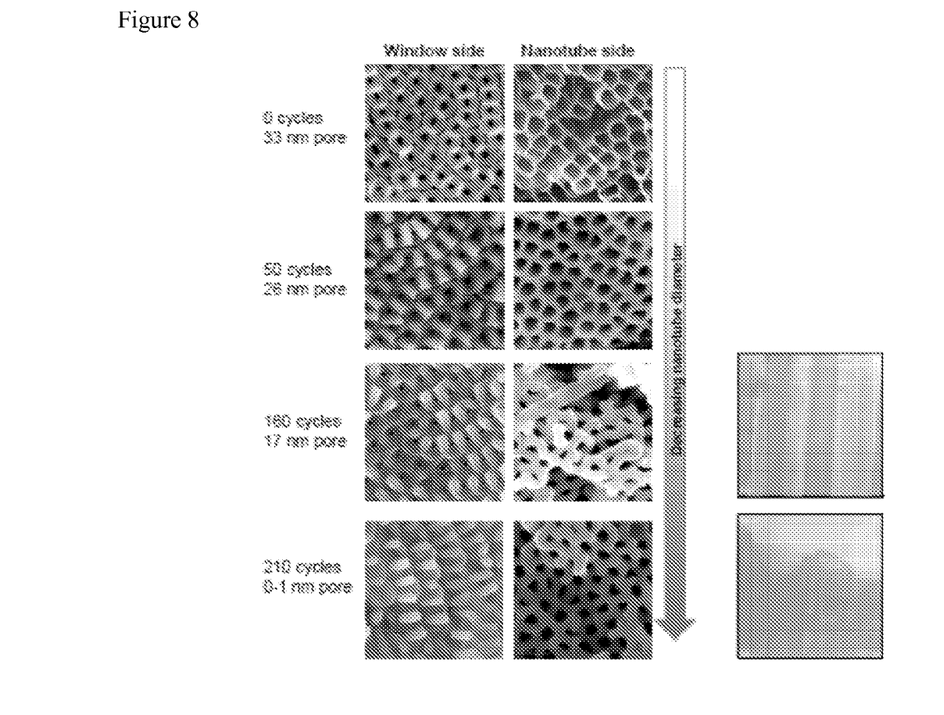
FIG. 8 shows one embodiment of customization to produce various pore sizes.
Figure 9A:
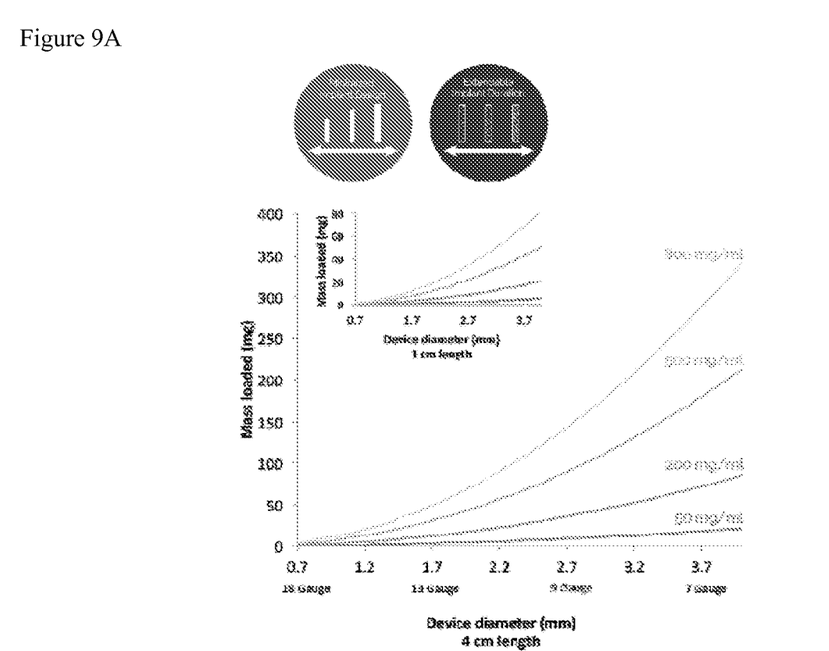
FIG. 9A and FIG. 9B show one embodiment of pore size effect.
Figure 9B:
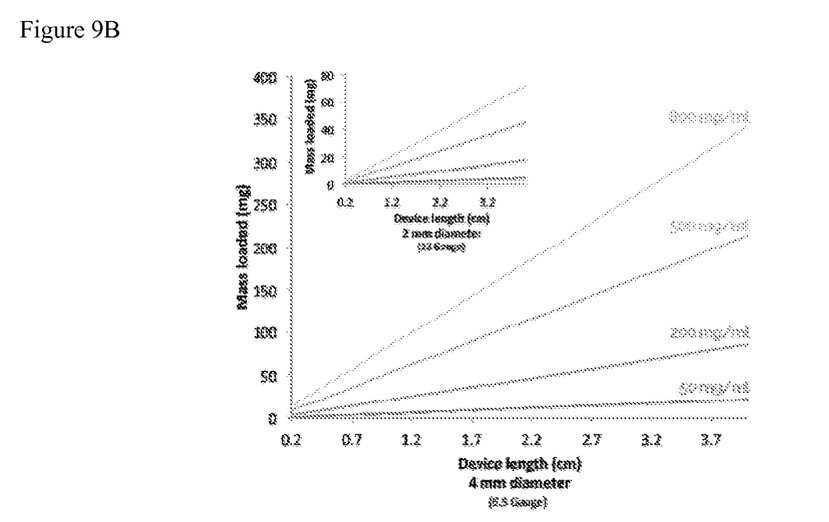
Figure 10A:
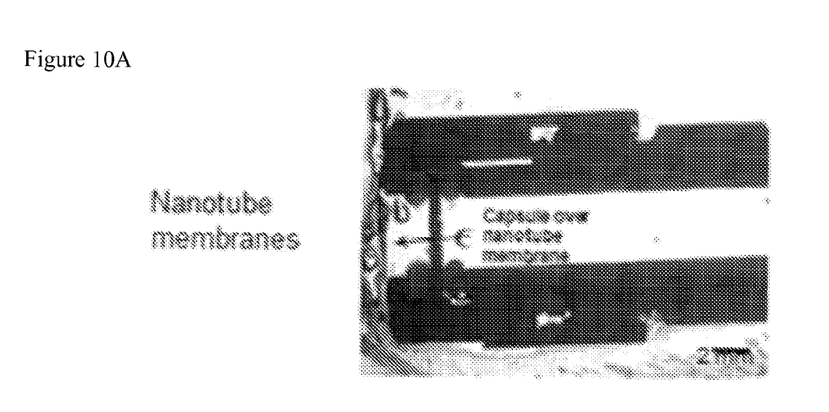
FIG. 10A and FIG. 10B show one embodiment of in vivo results.
Figure 10B:
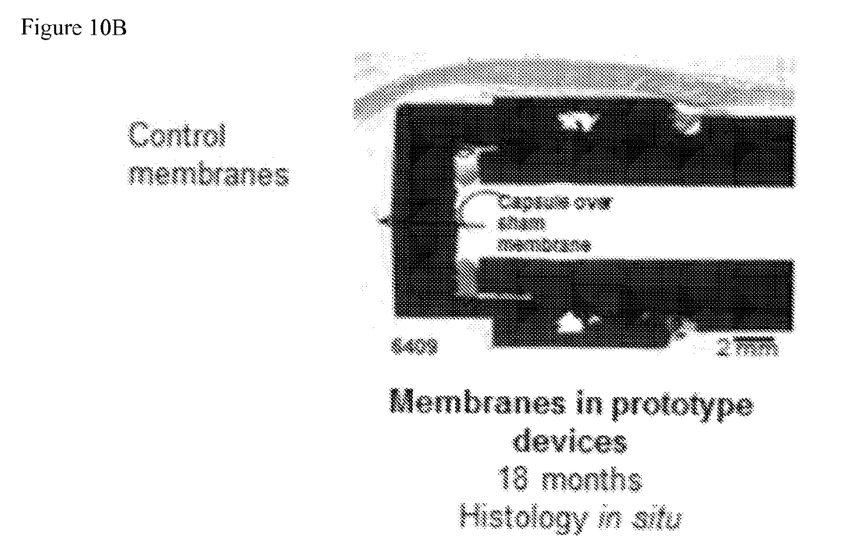
Figure 11A:
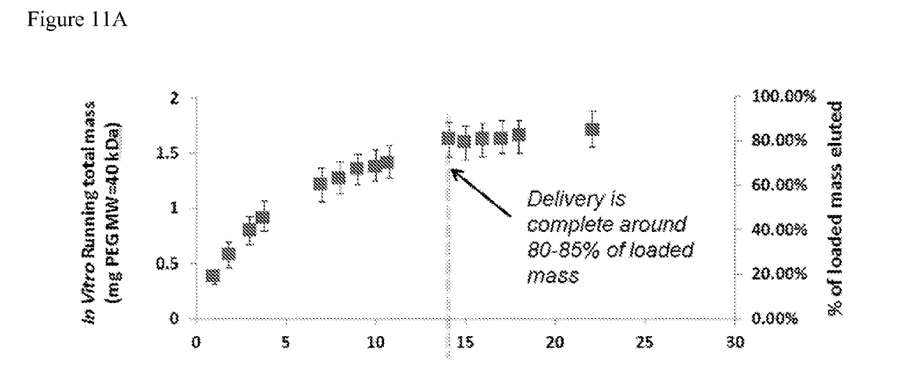
FIG. 11A and FIG. 11B show one embodiment of the present invention.
Figure 11B:
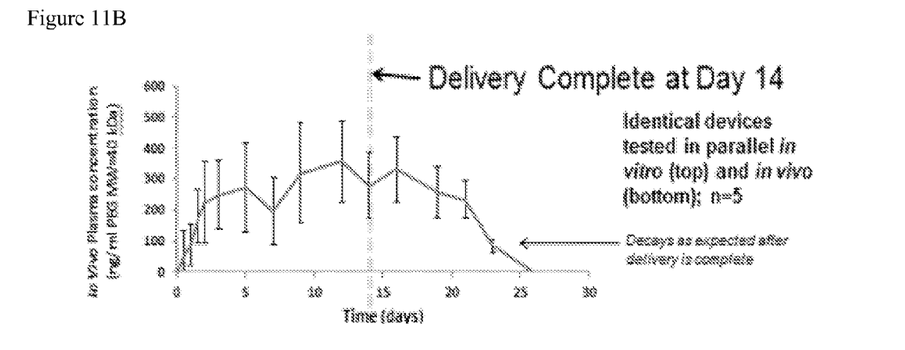
Figure 12:
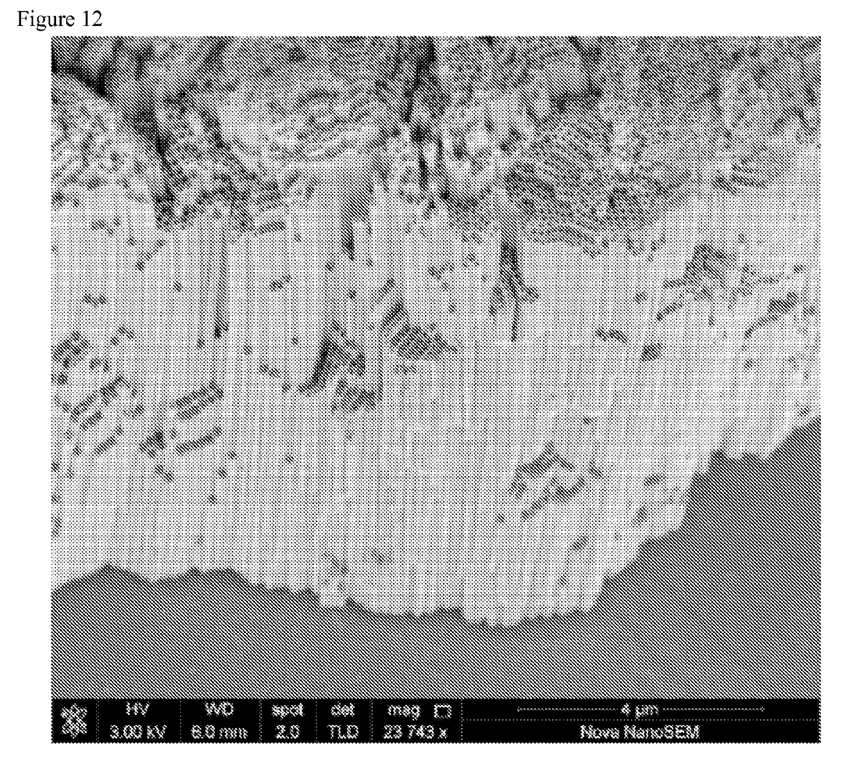
FIG. 12 shows one embodiment of the present invention.
Figure 15A:
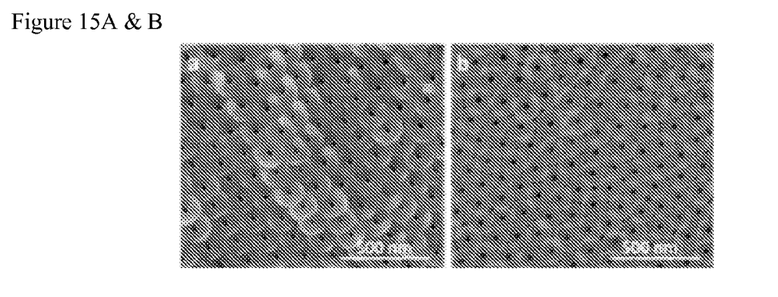
FIGS. 15A and B show 15-25 nm and 35-45 nm inner diameter.
Figure 16A:
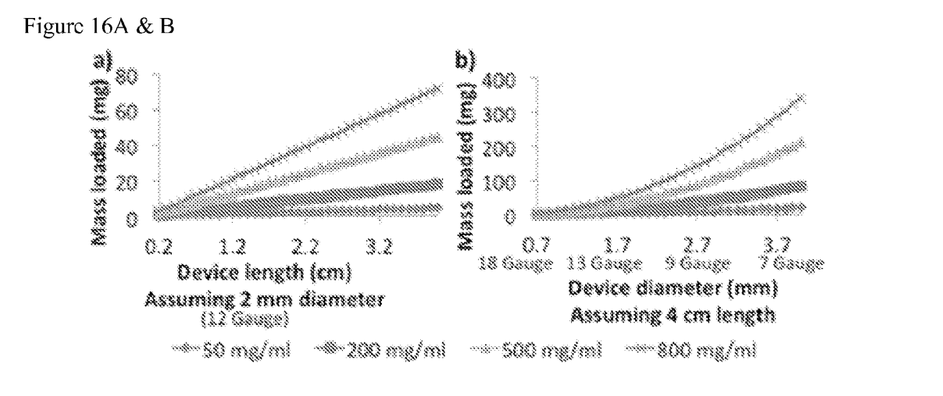
Figure 17:
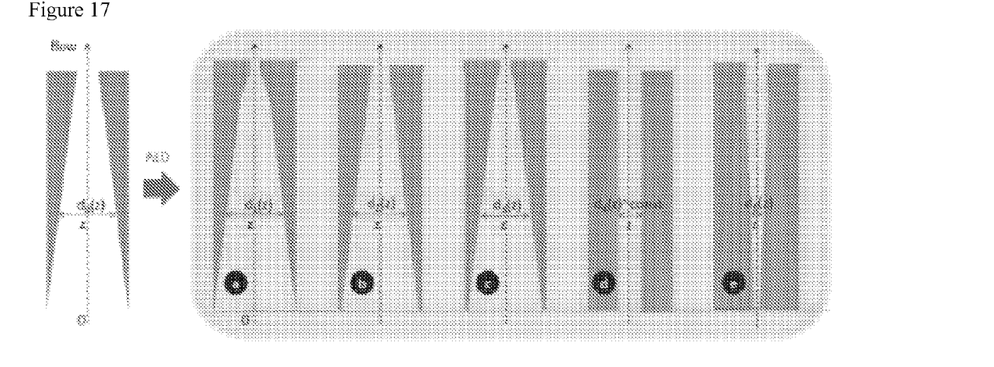
FIG. 17 shows the control of coating geometry that is available for the method of the present invention. For example, merely a portion of the interior of the nanopores can be coated (a), or all of the interior can be coated to various thicknesses with increasing coating time (b-e).
Figure 18:
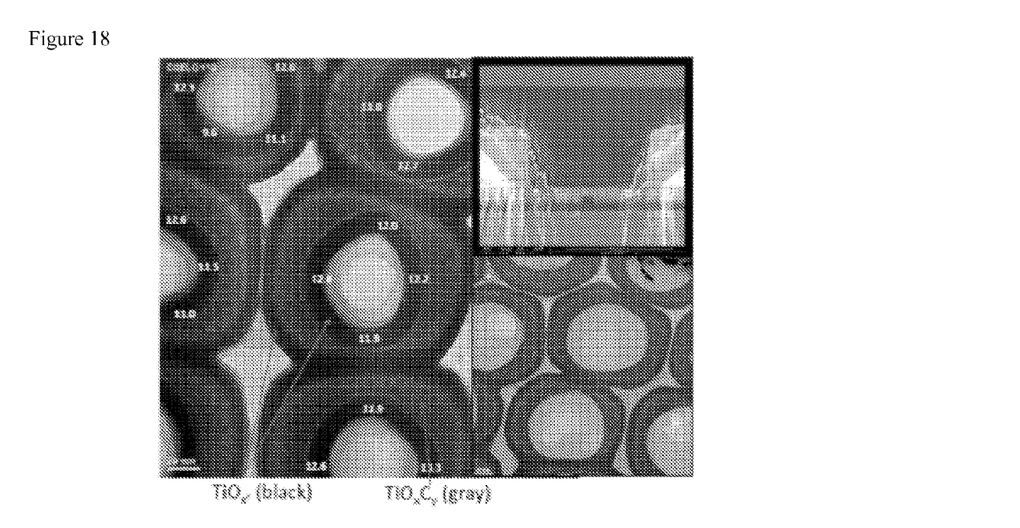
FIG. 18 shows coated nanopores prepared by the method of the present invention, with the black areas indicated as resulting from the coating process. The coating layer is pure titania ($TiO_x$) while the nanopore prior to coating is $TiO_xC_y$. In the post-ALD TEM image, Ti:O:C atomic ratio is 26.4:73.6:0. Before ALD, the inner gray and outer black portions of nanopores shows Ti:O:C atomic ratio is 21.3:62.8:15.9 and 26.5:73.5:0, respectively. Even before the ALD coating, the carbon incorporation may be zero and vary depending on samples.
Figure 19:
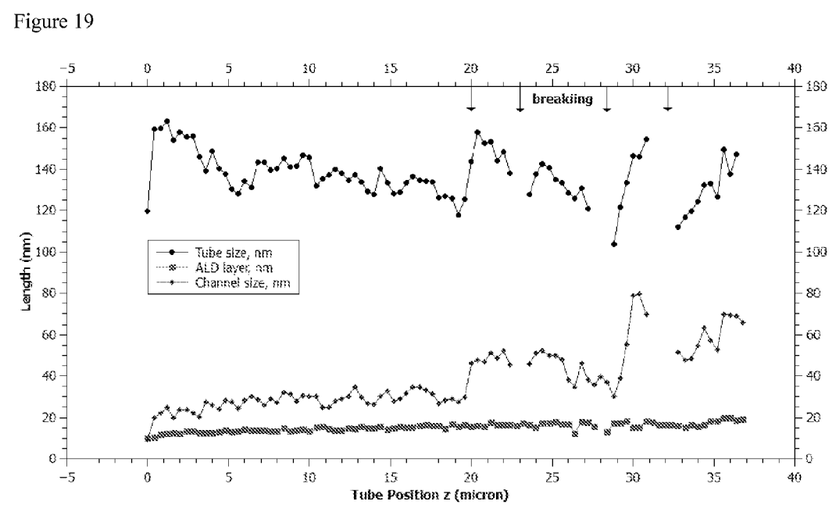
FIG. 19 shows tube position v. length for tube size, Atomic Layer Deposition (ALD) layer, and channel size.
Figure 20:
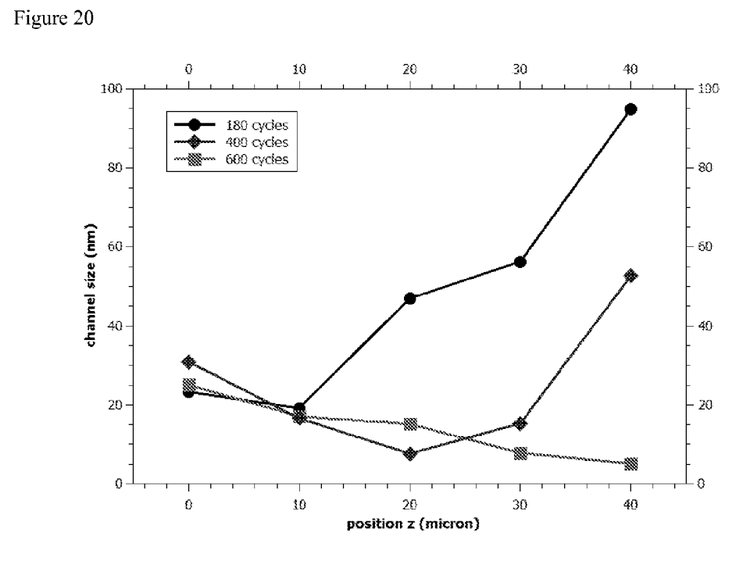
FIG. 20 shows position versus channel size for methods involving 180, 400 and 600 cycles.

Pores were produced from 0.1 nm to 50 nm in diameter by varying the ALD cycle number. Deposition can be designed to coat the surface evenly, with less than 1 nm variation in an 11.8 nm coating over many microns. This achieves a coating aspect ratio of greater than $10^4$, with the coating aspect ratio defined as the length of the coating over the variation in coating thickness (see FIG. 8 and FIGS. 15A & B, TEM images).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a coated nanoporous membrane comprising a plurality of nanopores, wherein each nanopore has a first open end and an interior, the method comprising:
   forming a reaction mixture under vapor deposition conditions in a reaction chamber wherein the reaction mixture comprises a coating agent and the nanoporous membrane, wherein the vapor deposition conditions are Atomic Layer Deposition conditions comprising a temperature of from about room temperature to less than 100° C.,
   such that a portion of the interior of each nanopore is coated with the coating agent to form a coating layer.

2. The method of claim 1, wherein the Atomic Layer Deposition conditions comprise a temperature of from about 50° C. to less than 100° C.

3. The method of claim 1, wherein the coating agent comprises tetrakis(dimethylamido)titanium (TDMAT).

4. The method of claim 3, wherein the coating layer comprises titania.

5. The method of claim 1, wherein the plurality of nanopores comprises titania.

6. The method of claim 5, wherein the titania is substantially amorphous.

7. The method of claim 1, wherein the plurality of nanopores nanotubes such that the nanoporous membrane is a nanotube membrane.

8. The method of claim 7, wherein at least 10% of each nanotube interior is coated.

9. The method of claim 7, wherein at least 50% of each nanotube interior is coated.

10. The method of claim 7, wherein at least 75% of each nanotube interior is coated.

11. The method of claim 7, wherein the plurality of nanotubes before the forming step have an internal diameter of between 10 nm to 100 nm.

12. The method of claim 7, wherein the plurality of nanotubes after the forming step have an internal diameter of between 1 nm to 100 nm.

13. The method of claim 7, wherein the nanotube membrane is in contact with a substrate.

14. The method of claim 13, wherein the substrate comprises titanium.

15. The method of claim 1, further comprising:
   purging the reaction chamber of the coating agent; and
   repeating the forming step.

16. The method of claim 1, wherein the coated nanotube membrane is a titania nanotube membrane comprising a plurality of titania nanotubes, the method comprising:
   forming the reaction mixture under Atomic Layer Deposition conditions in the reaction chamber wherein the reaction mixture comprises the coating agent tetrakis (dimethylamido)titanium (TDMAT), and a titania nanotube membrane on a titanium substrate, such that at least a portion of the interior of the titania nanotube is coated with the titania coating agent to form the titania coating layer.

17. The method of claim 16, further comprising forming a second reaction mixture under Atomic Layer Deposition conditions comprising a second coating agent and the nanoporous membrane, such that a portion of the interior of a second nanopore is coated with the second coating agent.

18. A nanopore comprising a coated interior portion, prepared by the method of claim 1.

19. A nanopore membrane comprising:

a plurality of nanopores, each nanopore having a first open end and an interior, wherein at least one nanopore comprises a coating layer on a portion of the interior, wherein the coated interior is prepared by the method of claim 1.

20. A device comprising:

a capsule suitable for implantation;

a reservoir encapsulated by the capsule, wherein the reservoir is suitable for containing a therapeutic agent; and a nanopore membrane attached to the capsule such that the nanopore membrane is in contact with the reservoir, wherein the nanopore membrane comprises a plurality of nanopores in fluid contact with the reservoir, wherein the nanopores have an interior with a coating layer on at least a portion of the interior, such that the plurality of nanopores is a diffusion pathway out of the reservoir for the therapeutic agent.

21. The device of claim 20, wherein the plurality of nanopores is the only diffusion pathway out of the reservoir for the therapeutic agent.

22. A titania composition comprising a titanium substrate;

an amorphous titania layer on the titanium substrate, wherein the titania layer comprises $TiO_xC_y$, wherein subscript x is from about 1.5 to about 4.0, and subscript y is from 0 to about 1.0; and at least one layer of $TiO_x$ chemically bound to the amorphous titania layer, wherein subscript x is from about 1.5 to about 4.0.

* * * * *